United States Patent [19]

Calderó Ges et al.

[11] Patent Number: 4,515,806

[45] Date of Patent: May 7, 1985

[54] FURAN DERIVATIVES AND ADDITION SALTS THEREOF PHARMACEUTICAL COMPOSITIONS AND THE THERAPEUTICAL APPLICATIONS THEREOF

[75] Inventors: José M. Calderó Ges; Eusebio M. Fabá, both of Barcelona, Spain

[73] Assignee: Inke, S.A., Barcelona, Spain

[21] Appl. No.: 478,052

[22] Filed: Mar. 23, 1983

[30] Foreign Application Priority Data

Apr. 16, 1982 [ES] Spain .................................. 511.896
May 21, 1982 [ES] Spain .................................. 512.419
Jan. 26, 1983 [ES] Spain .................................. 519.286
Jan. 26, 1983 [ES] Spain .................................. 519.287

[51] Int. Cl.³ ...................... A61K 31/34; C07D 307/52
[52] U.S. Cl. .................................... 514/471; 549/495; 514/925
[58] Field of Search ...................... 549/495; 424/285

[56] References Cited

U.S. PATENT DOCUMENTS 4,112,234  9/1978  Crenshaw et al. ................... 548/342
4,203,909  5/1980  Algieri et al. ..................... 424/285 X
4,279,819  7/1981  Price et al. ....................... 549/495 X

OTHER PUBLICATIONS

Judd et al., Chemical Abstracts, vol. 92 (1980) 22376d.
Price et al., Chemical Abstracts, vol. 90 (1979) 87257u.
Judd et al., Chemical Abstracts, vol. 96 (1982) 35069p.
Drugs of the Future, vol. I (1) 13 (1982).
Algieri et al., Chemical Abstracts, vol. 93 (1980) 150244s.
Pioch, Chemical Abstracts, vol. 97 (1982) 72354u.
Drugs of the Future, vol. V (6) 295 (1980).
The Merck Index, 9th edition (1976), No. 36.
The Merck Index, 9th edition (1976), No. 59.

*Primary Examiner*—Richard L. Raymond
*Attorney, Agent, or Firm*—Bell, Seltzer, Park & Gibson

[57] ABSTRACT

New furan derivatives and the addition salts thereof having the formula:

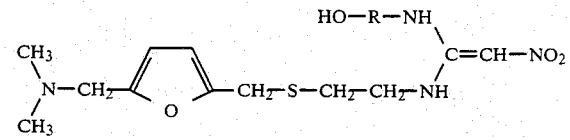

where R is a straight or branched alkylene chain having 1 to 6 carbon atoms, the processes for the preparation of said derivatives and the salts thereof and the pharmaceutical compositions containing them. These furan derivatives and the addition salts thereof are applicable for the treatment of gastroduodenal ulcer and all syndromes sustained or accompanied by acid secretion.

5 Claims, 1 Drawing Figure

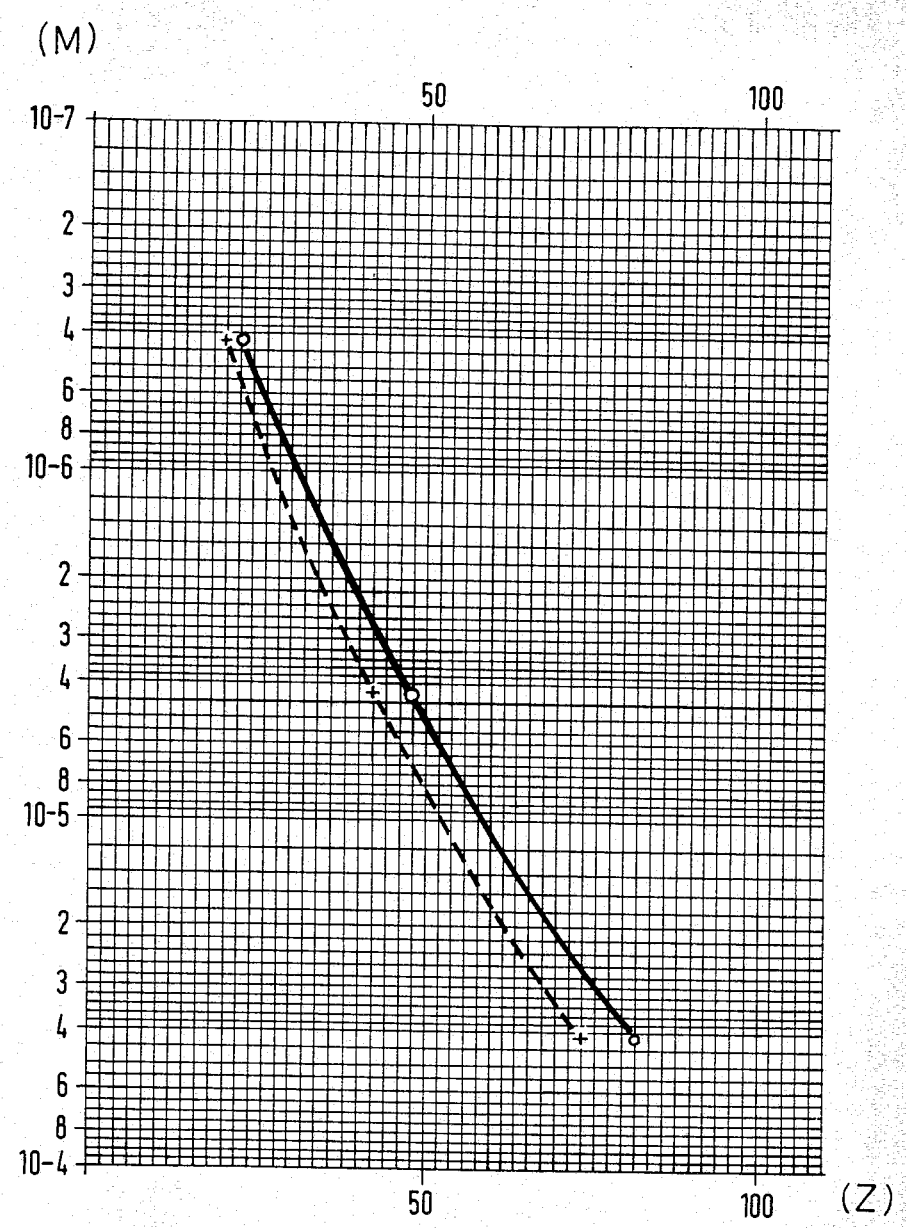

FURAN DERIVATIVES AND ADDITION SALTS THEREOF PHARMACEUTICAL COMPOSITIONS AND THE THERAPEUTICAL APPLICATIONS THEREOF

FIELD OF THE INVENTION

This invention relates to new furan derivatives having interesting therapeutic indications in clinics, such as the treatment of gastroduodenal ulcer and all syndromes sustained or accompanied by acid secretion, to processes for the preparation thereof and of the physiologically acceptable salts thereof, to pharmaceutical compositions containing said derivatives and/or the salts thereof and to the therapeutical application of said compositions.

SUMMARY OF THE INVENTION

The invention provides compounds having the general formula

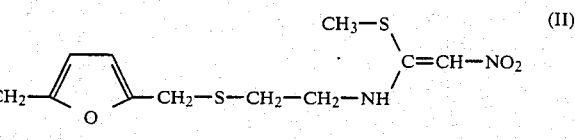

(I)

and the physiologically acceptable salts thereof, where R is a straight or branched alkylene chain of 1 to 6 carbon atoms.

Included among the physiologically acceptable salts are those formed with inorganic acids such as hydrochloric, hydrobromic and sulphuric acids or with organic mono and dicarboxylic acids such as acetic, oxalic, malic, fumaric, etc. acids.

The compounds and the salts thereof may be administered orally or parenterally.

In the pharmaceutical compositions, these compounds are generally accompanied by appropriate vehicles. The pharmaceutical forms for oral administration may be capsules, tablets or syrups.

The daily dosage for oral administration is 100 mg to 1.2 g of active ingredient, in form of unit doses containing from 20 to 200 mg.

Parenteral administration may be by injections at intervals or by continuous infusion. The injection solutions may contain from 10 to 100 mg/ml of active ingredient.

The active ingredients may be associated with other therapeutic agents depending on the specific conditions of the affection being treated.

All the formula (I) compounds may be tautomeric and the formula is intended to cover all the tautomers. There may also be optical isomers and the formula is intended to cover all the optical diastereoisomers and enantiomers.

The preferred process for the preparation of the compounds of the invention consists of reacting a compound of formula

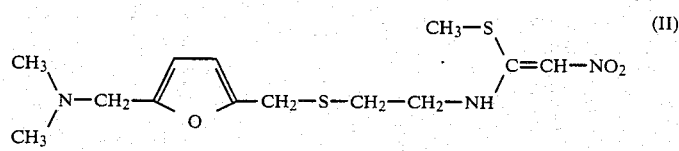

with a hydroxyalkylamine of the general formula $$HO-R-NH_2 \quad (III)$$

where R has the meaning expressed above, in an appropriate solvent medium.

The chemical reaction taking place in the said process may be expressed schematically as follows:

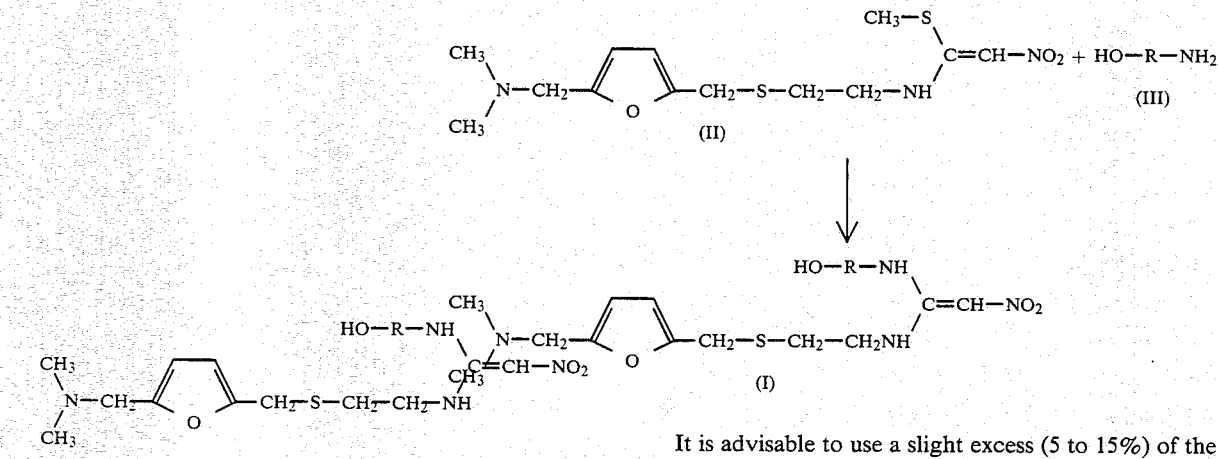

It is advisable to use a slight excess (5 to 15%) of the hydroxyalkylamine over the 1:1 mole ratio of the stoichiometric reaction in an appropriate solvent medium such as methanol, isopropanol, chloroform, etc, or mixtures thereof.

The process is conducted at temperatures lying between 0° C. and the boiling point of the solvent used, the 40° to 70° C. range being advisable.

The product obtained, which is isolated from the reaction medium by conventional methods, may be purified in the normal way by crystallisation in a solvent, e.g., isopropanol, acetonitrile, ethyl acetate, etc. or mixtures thereof.

In a further process for the preparation of compounds of the general formula (I), a compound of the general formula

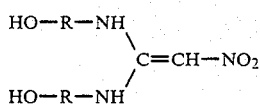 (IV)

where both R must be identical and have the meaning expressed hereinbefore is reacted with a compound of formula

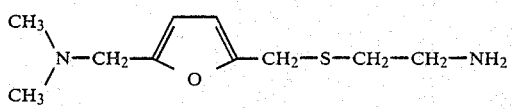 (V)

in an appropriate solvent medium.

In a further process for the preparation of compounds of the general formula (I), the foregoing compound of general formula

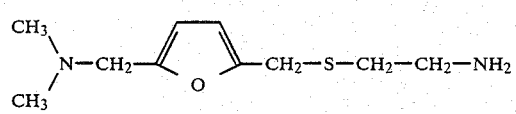 (V)

is reacted with a compound of general formula

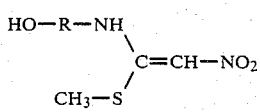 (VI)

where R has the meaning expressed hereinbefore.

The formula (IV) products may be prepared conventionally by reacting the corresponding hydroxyalkylamine (III) with 1,1-bis(methylthio)-2-nitroethene.

The compounds of the general formula (I) may also be prepared by reacting a compound of formula

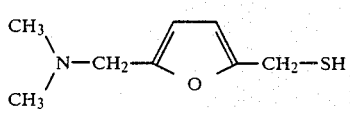 (VII)

with a compound of the general formula (VIII) where X is a halogen

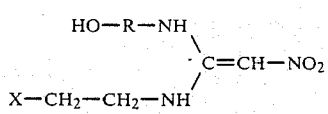 (VIII)

or a compound of the general formula

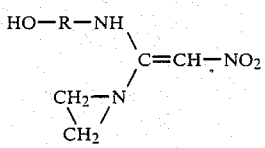 (IX)

Likewise the compounds of the general formula (I) may also be prepared by reacting a compound of the general formula

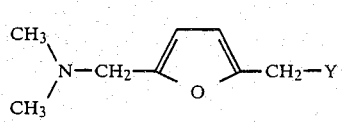 (X)

where Y, preferably being halogen, may also be —OH or acyl, with a compound of the general formula

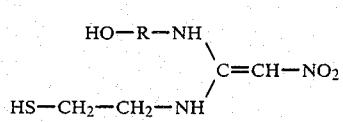 (XI)

or a metal salt thereof, such as the Ag, Cu, Zn or Pb salt.

Finally, the compounds of general formula (I) may also be prepared by reacting nitromethane with a compound of the general formula

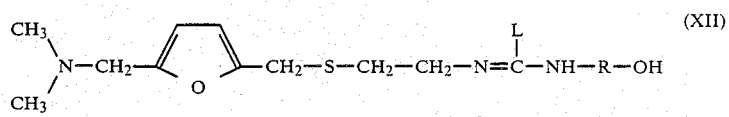 (XII)

where L is a leaving group. Examples of leaving groups are groups of formula —SR', —OR', etc. where R' is a straight or branched alkyl chain of 1 to 6 carbon atoms, optionally substituted with a phenol group.

Some specific, illustrative and non-limitative examples of the object of the invention are described hereinbelow.

EXAMPLE 1

(a) 12.2 g (0.2 mole) of 2-aminoethanol were added slowly over a period of 1 hour to a solution of 33.1 g (0.1 mole) of N-[2-[[(5-[dimethylamino)methyl]-2-furanyl)methyl]thio]ethyl]-1-methylthio-2nitro-1-etheneamine in 100 ml of isopropanol. After the addition, the mixture was held at 35° C. for 5 hours, the solvent was evaporated off under vacuum, 50 ml of water were added, followed by extraction with chloroform (2×50 ml). The organic extract was dried, treated with activated carbon, filtered and concentrated to dryness, to give 28 g of N-[2-[[(5-[(dimethylamino)methyl]-2-furanyl)methyl]thio]ethyl]-N'-(2-hydroxyethyl)-2-nitro-1,1-ethenediamine of the formula

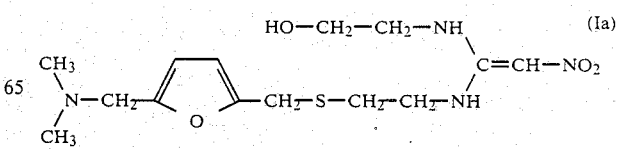 (Ia)

in the form of a yellowish oil which is recrystallised from isopropyl alcohol to give 25 g of a crystalline white solid, soluble in methanol and chloroform, m.p. 108°–109° C. and showing absorption maxima in the ultraviolet range at 230 and 320 nm. The IR spectrum shows the following bands among the most characteristic and significant: 3400, 3150, 2950, 2830, 2790, 1620, 1560, 1460, 1405, 1385, 1350, 1220, 1180, 1130, 1060, 1050, 1010, 980, 940, 900, 820, 800, 760 cm$^{-1}$.

Elemental analysis: $C_{14}H_{24}N_4O_4S$ (m.w.: 344.44). % Calculated: C: 48.8%; H: 7.02%; N: 16.26%; S: 9.30%. % Found: C: 48.7%; H: 7.1%; N: 17.1%; S: 9.18%.

(b) a 20 g sample of N-[2-[[(5-[(dimethylamino)methyl]-2-furanyl)methyl]thio]ethyl]-N'-(2-hydroxyethyl)-2-nitro-1,1-ethenediamine (58 mmoles) was dissolved in 100 ml of ethanol (99–100%) and there were added slowly 25 ml of isopropyl alcohol containing 58 mmoles of hydrochloric acid. The mixture was left under stirring overnight and the solid precipitate was filtered, washed with ethanol and dried to give 18 g of N-[2-[[(5-[(dimethylamino)methyl]-2-furanyl)methyl]thio]ethyl]-N'-(2-hydroxyethyl)-2-nitro-1,1-ethenediamine hydrochloride, in the form of white crystals, soluble in water and methanol, m.p. 119°–122° C.

The I.R. spectrum showed the following bands among the most characteristic and significant: 3600–2500, 1610, 1570, 1460, 1410, 1340, 1225, 1040, 1005, 970, 930, 795, 750 and 695 cm$^{-1}$.

Elemental analysis: $C_{14}H_{25}ClN_4O_4S$ (m.w.: 380.89). % Calculated: C: 44.14%; H: 6.61%; N: 14.7%; S: 8.41%. % Found: C: 44.31%; H: 6.8%; N: 14.4%; S: 8.6%.

EXAMPLE 2

78 ml of 2-aminoethanol (1.3 moles) were added slowly over half an hour to a solution of 95 g of 1,1-bis(methylthio)-2-nitroethene (0.57 mole) in 500 ml of toluene at 80° C. After the addition, the mixture was held at 80° C. for half an hour, was cooled to room temperature and the solid formed was filtered off, washed with chloroform (2×100 ml portions) and was dried to give 107 g N,N'-bis(2-hydroxyethyl)-2-nitro-1,1-ethenediamine (97–98% yield) in yellowish crystal form. m.p. 145°–146° C.

A sample of the above solid, recrystallised from water and methanol, exhibited the following physical and chemical properties:

White crystals, m.p. 148°–149° C., slightly soluble in methanol and ethanol, soluble in water. The methanol solution gives a maximum at 320 nm.

The I.R. spectrum (KBr tablet) exhibited the following bands among the characteristic and significant: 3300, 3000, 2920, 1620, 1580, 1480, 1400, 1350, 1290, 1260, 1220, 1060, 1010, 870, 825, 760, 730, 695 and 660 cm$^{-1}$.

Elemental analysis: $C_6H_{13}N_3O_4$ (m.w.: 191.19). % Calculated: C: 37.69%; H: 6.85%; N: 21.97%. % Found: C: 37.50%; H: 6.79%; N: 21.82%.

EXAMPLE 3

The following compounds were prepared in a similar way from the corresponding hydroxyalkylamines by the process described in Example 2.

(a) (±)-N,N'-bis(2-hydroxypropyl)-2-nitro-1-ethenediamine.
m.p.: 129°–131° C.
I.R.: 3250, 2950, 2920, 1610, 1570, 1460, 1400, 1260, 1210, 1120, 1080, 1000, 930, 910, 840, 750, 690 cm$^{-1}$.

Elemental analysis: $C_8H_{17}N_3O_4$ (m.w. 219.24) % Calculated: C: 43.83%; H: 7.81%; N: 19.17%. % Found: C: 43.90%; H: 7.78%; N: 19.14%.

(b) N,N'-bis(3-hydroxypropyl)-2-nitro-1,1-ethenediamine.
m.p. 94°–96° C.
I.R.: 3300, 2940, 2850, 1605, 1570, 1460, 1400, 1340, 1250, 1210, 1190, 1050, 1030, 1000, 940, 740, 690 cm$^{-1}$.

Elemental analysis: $C_8H_{17}N_3O_4$ (m.w. 219.24). % Calculated: C: 43.83%; H: 7.81%; N: 19.17%. % Found: C: 43.78%; H: 7.88%; N: 19.05%.

(c) (±)-N,N'-bis[(1-hydroxymethyl)-propyl]-2-nitro-1,1-ethenediamine.
m.p.: 135°–136° C.
I.R.: 3250, 2950, 2860, 1600, 1580, 1420, 1350, 1240, 1200, 1150, 1110, 1040, 1000, 940, 920, 840, 760, 690, 630 cm$^{-1}$.

Elemental analysis: $C_{10}H_{21}N_3O_4$ (m.w. 247.30). % Calculated: C: 48.57%; H: 8.56%; N: 17.00%. % Found: C: 48.49%; H: 8.63%; N: 16.92%.

(d) (−)-N,N'-bis[(1-hydroxymethyl)-propyl]-2-nitro-1,1-ethenediamine.
m.p.: 133°–135° C.
I.R.: 3250, 2950, 2930, 2860, 1600, 1580, 1460, 1410, 1345, 1245, 1200, 1150, 1005, 995, 940, 910, 750, 690, 630 cm$^{-1}$.

Elemental analysis: $C_{10}H_{21}N_3O_4$ (m.w. 247.30). % Calculated: C: 48.57%; H: 8.56%; N: 17.00%. % Found: C: 48.62%; H: 8.50%; N: 17.13%.

EXAMPLE 4

21.5 g (0.1 mole) 2-[[[(5-dimethylamino)methyl-2-furanyl]methyl]thio]ethanamine were added slowly over 1 hour over a solution of 21.96 g (0.115 mole) N,N'-bis(2-hydroxyethyl)-2-nitro-1,1-ethenediamine in 100 ml water at 80° C. in a round bottom flask fitted with stirring and reflux system. After the addition, the resulting mixture was held under reflux for 3 hours. It was then cooled and extracted with chloroform (200 ml plus 2×100 ml portions). The organic extract was evaporated to dryness and the residue was washed with toluene until the resulting oil gave a single Rf spot: 0.42 in thin layer chromatography (chloroform: methanol: ammonia, 75/25/1). The residue was dissolved in isopropyl alcohol, treated with activated carbon, was filtered and concentrated to dryness to give 20 g N-[2-[[(5-[(dimethylamino)methyl]-2-furanyl)methyl]thio]ethyl]-N'-(2-hydroxyethyl)-2-nitro-1,1-ethenediamine as a yellowish oil which is crystallised from isopropyl alcohol to give 17 g of a white solid having the same properties as the product prepared according to Example 1, paragraph (a).

EXAMPLE 5

The following compounds were prepared in a similar way following the processes described in Examples 1 and 4.

(a) (±)-N-[2-[[(5-[(dimethylamino)methyl]-2-furanyl)methyl]thio]ethyl]-N'-(2-hydroxypropyl)-2-nitro-1,1-ethenediamine hydrochloride.
m.p.: 119°–121° C.
I.R.: 3700–2500, 1610, 1570, 1460, 1400, 1350, 1230, 1130, 1010, 975, 935, 800, 755, 695 cm$^{-1}$.

Elemental analysis: $C_{15}H_{26}N_4O_4S \cdot HCl$ (m.w. 394.92). % Calculated: C: 45.62%; H: 6.89%; N: 14.19%; S: 8.12%. % Found: C: 45.49%; H: 6.78%; N: 14.23%; S: 8.18%.

(b) N-[2-[[(5-[(dimethylamino)methyl]-2-furanyl)methyl]thio]ethyl]-N'-(3-hydroxypropyl)-2-nitro-1,1-ethenediamine hydrochloride.

m.p.: 80°–82° C.

I.R.: 3700–2500, 1605, 1570, 1460, 1400, 1350, 1225, 1120, 1005, 970, 930, 790, 750, 690 cm$^{-1}$.

Elemental analysis: $C_{15}H_{26}N_4O_4S \cdot HCl$ (m.w. 394.92). % Calculated: C: 45.62%; H: 6.89%; N: 14.19%; S: 8.12%. % Found: C: 45.45%; H: 6.71%; N: 14.10%; S: 7.98%.

(c) (±)-N-[2-[[(5-[(dimethylamino)methyl]-2-furanyl)methyl]thio]ethyl]-N'-](1-hydroxymethyl)propyl]-2-nitro-1,1-ethenediamine hydrochloride.

m.p.: 98°–102° C.

I.R.: 3700–2500, 1605, 1575, 1470, 1410, 1360, 1305, 1240, 1200, 1135, 1045, 1015, 980, 945, 870, 800, 760, 700, 630, 600 cm$^{-1}$.

Elemental analysis: $C_{16}H_{28}N_4O_4S \cdot HCl$ (m.w. 408.95). % Calculated: C: 47.00%; H: 7.15%; N: 13.70%; S: 7.84%. % Found: C: 47.15%; H: 7.02%; N: 13.61%; S: 7.77%.

(d) (−)-N-[2-[[(5-[(dimethylamino)methyl]-2-furanyl)methyl]thio]ethyl]-N'-[(1-hydroxymethyl)propyl]-2-nitro-1,1-ethenediamine hydrochloride.

m.p.: 99°–103° C.

I.R.: 3700–2450, 1605, 1575, 1470, 1410, 1360, 1305, 1240, 1200, 1135, 1045, 1015, 980, 945, 870, 800, 760, 700, 630, 600 cm$^{-1}$.

Elemental analysis: $C_{16}H_{28}N_4O_4S \cdot HCl$ (m.w. 408.95). % Calculated: C: 47.00%; H: 7.15%; N: 13.70%; S: 7.84%. % Found: C: 47.15%; H: 7.02%; N: 13.61%; S: 7.77%.

EXAMPLE 6

21.5 g (0.1 mole) of 2-[[[(5-dimethylamino)methyl-2-furanyl]methyl]thio]-ethanamine were added slowly over 1 hour over a solution of 17.8 g (0.1 mole) of N-(hydroxyethyl)-1-methylthio-2-nitro-1-etheneamine in 60 ml water. After the addition, the mixture was held at 35° C. for 8 hours. It was extracted with chloroform (2×50 ml) and the organic extract was dried over anhydrous MgSO$_4$, treated with activated carbon, filtered and concentrated to dryness, to give 26 g of N-[2-[[(5-[(dimethylamino)methyl]-2-furanyl)methyl]thio]ethyl]-N'-(2-hydroxyethyl)-2-nitro-1,1-ethenediamine as a yellowish oil which is crystallised from isopropyl alcohol to give 23 g of a crystalline white solid having the same properties as the product prepared according to Example 1, paragraph (a).

EXAMPLE 7

A solution of 2.24 g (40 mmoles) of potassium hydroxide in 15 ml water was added slowly over a stirred solution of 2.61 g (10 mmoles) of 5-[(dimethylamino)methyl]-2-furanmethanethiol oxalate (1:1) and 2.09 g (10 mmoles) of N-(2-chloroethyl)-N'-(2-hydroxyethyl)-2-nitro-1,1-ethenediamine in 20 ml water at 45° C. under nitrogen atmosphere. The solution was stirred at 45° C. for 2½ hours and at room temperature for 15 hours. Air was bubbled through the mixture for 15 minutes, it was extracted with ether (2×15 ml) and the aqueous fraction was evaporated under vacuum. Tetrahydrofurane (70 ml), an excess of anhydrous sodium carbonate and activated carbon were added to the residue. It was filtered, the organic phase was decanted off and concentrated under vacuum, to give 1.9 g of a yellowish oil which was crystallised from isopropyl alcohol-ethyl ether to give 1.3 g of N-[2-[[(5-[(dimethylamino)methyl]-2-furanyl)methyl]thio]ethyl]-N'-(2-hydroxyethyl)-2-nitro-1,1-ethenediamine having the same properties as the product prepared according to Example 1, paragraph (a).

EXAMPLE 8

Ethyl ether (15 ml) and an excess of anhydrous sodium carbonate were added to a mixture in water of 0.13 g (0.5 mmole) of 5-[(dimethylamino)methyl]-2-furanmethanethiol oxalate (1:1), sodium dithionite (0.05 g) and anhydrous sodium carbonate (0.15 g). The mixture was filtered and the filtrate was evaporated under vacuum. 0.087 g (0.5 mmole) of N-(2-hydroxyethyl)-alpha-(nitromethylene)-1-aziridinemethaneamine and 4 ml of methanol were added to the residue. The mixture was evaporated to dryness and the residue was heated to 95°–100° C. for 1 hour and chromatographed over silica (methanol-0.88 NH$_3$; 79:1). The appropriate eluate was evaporated under vacuum to give 0.12 g of N-[2-[[(5-[(dimethylamino)methyl]-2-furanyl)methyl]thio]ethyl]-N'-(2-hydroxyethyl)-2-nitro-1,1-ethenediamine having the same properties as the product prepared according to Example 1, paragraph (a).

EXAMPLE 9

A solution of 2 g of N-[2-[[(5-[dimethylamino)methyl]-2-furanyl)methyl]thio]ethyl]-N'-(2-hydroxyethyl)-S-methylisothiourea in 8 g of nitromethane was heated for 22 hours at 98°–100° C. The mixture was evaporated under vacuum and the oily residue was dissolved in 10 ml of isopropyl alcohol, was treated with activated carbon, was filtered and was cooled to 5° C., to precipitate 1.3 g of N-[2-[[(5-[(dimethylamino)methyl]-2-furanyl)methyl]thio]ethyl]-N'-(2-hydroxyethyl)-2-nitro-1,1-ethenediamine having the same properties as the product prepared according to Example 1, paragraph (a).

EXAMPLE 10

A solution of 2.24 g (40 mmoles) of potassium hydroxide in 15 ml water was added slowly over a stirred solution of 2.1 g (10 mmoles) of 5-[(dimethylamino)methyl]-2-chloromethylfuran hydrochloride and 2.07 g (10 mmoles) of N-(2-hydroxyethyl)-N'-(2-mercaptoethyl)-2-nitro-1,1-ethenediamine in 10 ml water at 45° C. under nitrogen atmosphere. The solution was stirred at 45° C. for 2 hours and at room temperature for 5 hours. Air was bubbled through the mixture for 15 minutes, it was extracted with ether and the aqueous phase was extracted with chloroform (2×25 ml). The chloroform extract was dried over anhydrous sodium sulphate, was treated with activated carbon, was filtered and concentrated under vacuum. The residue was dissolved in 8 ml isopropyl alcohol and was placed in a refrigerator. 0.9 g of N-[2-[[(5-[(dimethylamino)-methyl]-2-furanyl)methyl]thio]ethyl]-N'-(2-hydroxyethyl)-2-nitro-1,1-ethenediamine precipitated out. The product has the same properties as the product prepared according to Example 1, paragraph (a).

EXAMPLE 11

This example concerns the preparation of several pharmaceutical compositions containing the compound of Example 1, (b), N-[2-[[(5-[(dimethylamino)-methyl]-2-furanyl)methyl]thio]ethyl]-N'-(2-hydroxyethyl)-2-nitro-1,1-ethenediamine hydrochloride, as active ingredient.

(a) 1,000 gelatine no. 1 capsules, each containing 165.89 mg of the previously compacted compound (Example 1, (b)), were prepared.

The composition was as follows:

|  | For 1,000 capsules |
|---|---|
| Compound (Example 1, (b)) | 165.89 g |
| Microcrystalline cellulose | 54.11 g |
| Silicon dioxide | 3.00 g |
| Magnesium stearate | 2.00 g |

After sifting, the components were thoroughly mixed and the resulting powder was packed into the gelatine capsules in an appropriate filling machine.

(b) 1,000 tablets, each containing 165.89 mg of the compound (Example 1, b), were prepared from the following ingredients:

|  | For 1,000 tablets |
|---|---|
| Compound (Example 1, (b)) | 165.89 g |
| Microcrystalline cellulose | 118.11 g |
| Silicon dioxide | 12.00 g |
| Magnesium stearate | 4.00 g |

The previously compacted compound (Example 1, (b)) was mixed with the microcrystalline cellulose and the silicon dioxide and, thereafter, with the magnesium stearate. After homogenisation, the mixture was compressed in a press to form 1,000 tablets, each containing 165.89 mg of the compound (Example 1, (b)).

(c) Ten liters of syrup containing 165.89 mg of compound (Example 1, (b)), per each 5 c.c. dose, were prepared from the following ingredients:

|  | For 10 liters |
|---|---|
| Compound (Example 1, (b)) | 331.78 g |
| Sucrose | 7,000.00 g |
| Glycerine U.S.P. | 500.00 g |
| Sodium chloride | 80.00 g |
| Methyl-p-hydroxybenzoate | 10.00 g |
| Isopropyl-p-hydroxybenzoate | 2.00 g |
| Sorbic acid | 10.00 g |
| Sodium hydroxide | As required |
| Sweetener and flavouring | As required |
| Distilled water ad | 10 liters |

The methyl-p-hydroxybenzoate, isopropyl-p-hydroxybenzoate and sorbic acid were dissolved in a suitable amount of distilled water with gentle heating, together with the remaining substances, except the flavourings, which should be mixed in after the syrup has cooled and before the final topping up to 10 liters.

(d) 1,000 injectable ampoules, containing 55.29 mg of compound (Example 1, (b)) per each 5 c.c. dose, were prepared from the following ingredients:

|  |  |
|---|---|
| Compound (Example 1, (b)) | 55.29 g |
| Sodium chloride | 35.00 g |
| Water for injectables ad | 5 liters |

The compound (Example 1, (b)) and the sodium chloride were dissolved with stirring in a suitable amount of water for injectables, followed by topping up to 5 liters, filtering and sterilisation.

EXAMPLE 12

The pharmaceutical compositions of Example 11 were prepared in a similar way from the corresponding compounds of Example 5.

PHARMACOLOGICAL DESCRIPTION

The compounds of the invention have, mainly a histamine $H_2$ receptor blocking activity, inhibition of gastric acid secretion, protection of gastric ulcers. The toxicity is very low and the tolerance is good.

Rat Uterus $H_2$ Receptor Blocking Activity

This experiment was conducted to determine the selectivity of the Example 1, (b) product for the histamine $H_2$ receptors in comparison with ranitidine.

Rats in estrus were used and were administered 100 mcg of stilbestrol by intramuscular (i.m.) injection 30 hours before removing the uterus. On the day of the experiment, the uterine horn was removed and suspended in a De Jalon solution in an organ bath, held at 28° C. and aerated with a flow of 95% $O_2$ and 5% $CO_2$. Thereafter a sustained uterine contraction was induced by the addition of a KCl solution to provide a concentration in the organ bath of 4.2 mg/ml, namely, 10 times that of the De Jalon serum. The uterus was caused to relax with the addition of the amount of histamine required to obtain a good response.

The same experiment was conducted by adding the product of Example 1, (b) or the ranitidine before the histamine, the histamine then being added at the same rate as in the reference test.

$5.43 \times 10^{-5}$M histamine in the organ bath produced a 74.5% inhibition of the contraction caused by KCl.

The prior addition of the Example 1, (b) compound or ranitidine at different levels antagonised the histamine induced response in different degrees proportional to the concentration. The results obtained are given in the following table:

| | ANTAGONISM (% REDUCTION) OF THE HISTAMINE INDUCED RESPONSE IN KCl CONTRACTED RAT UTERUS | |
|---|---|---|
| CONCENTRATION IN ORGAN BATH | RANITIDINE HYDROCHLORIDE | EXAMPLE 1, (b) PRODUCT |
| $4.34 \times 10^{-8}$M | 0 | 0 |
| $4.34 \times 10^{-7}$M | 20% | 22.2% |
| $4.34 \times 10^{-6}$M | 42.2% | 47.3% |
| $4.34 \times 10^{-5}$M | 73.8% | 81.8% | and in the accompanying graph. wherein M is the concentration and Z is the antagonism (in % reduction).

From the results obtained, it is deduced that the effective concentration for producing a 50% antagonism of the histamine response ($EC_{50}$) is $5.5 \times 10^{-6}$M for the Example 1, (b) product and $8.25 \times 10^{-6}$M, for ranitidine under the above described experimental conditions.

With this trial, therefore, it was possible to show the selective effect of the Example 1, (b) product on the $H_2$ receptors of rat uterus and that the substance is more active than ranitidine, since the $EC_{50}$ thereof is 50% lower than that of ranitidine.

Ligature of Pylorus

The method of Visscher et al. (J. Pharmac. Exp. Ther., 110, 188, 1954) as indicated below was followed:

Male Wistar rats, weighing from 250 to 300 grams were used. The animals were split into lots of ten rats each and were fasted for 24 hours prior to starting the experiment, although they had free access to water.

The rats were anesthetised with ethyl ether, a laparotomy was performed and the pylorus was ligatured. The abdominal incision was then sewn.

Treatment was effected: (B-1) intravenously, through the femoral vein. (B-2) intraduodenally, prior to sewing the abdominal incision.

Three hours after ligature of the pylorus, the volumen of gastric juices was measured, the pH was determined by a Beckman Century SS-1 pH-meter.

The results obtained are given in Tables B-1 and B-2, and the total acidity thereof was determined by titration with 0,1N NaOH.

TABLE B-1

Volume, pH and total acidity (titration with 0,1N NaOH) percentage variation relative to control of the values corresponding to the animals treated intravenously with the Example 1, (b) product, ranitidine or cimetidine.

| PRODUCT | INTRAVENOUS DOSE (mg/kg) | RATS | VOLUME | pH | TOTAL ACIDITY |
|---|---|---|---|---|---|
| Example 1, (b) product | 10 | 3 | ↓ 51.9% | ↑ 263.2% | — |
|  |  | 5 | ↓ 62.6% | ↑ 119.2% | ↓ 89.2% |
|  |  | 8 | ↓ 0% | ↑ 134.4% | ↓ 78.2% |
| Ranitidine | 10 | 2 | ↓ 68.1% | ↑ 200.8% | — |
|  |  | 5 | ↓ 61.4% | ↑ 88.5% | ↓ 81.8% |
|  |  | 8 | ↓ 21% | ↑ 104.2% | ↓ 72.7% |
| Cimetidin | 10 | 2 | ↓ 41.0% | ↑ 50.4% | — |
|  |  | 5 | ↓ 23.2% | — | ↓ 11.7% |
|  |  | 8 | ↓ 7.3% | ↑ 64.9% | ↓ 52.7% |

TABLE B-2

Volume, pH and total acidity (titration with 0,1N NaOH), percentage variation relative to control of the values corresponding to the animals treated intraduodenally with the Example 1, (b) product, ranitidine or cimetidine.

| PRODUCT | INTRADUODENAL DOSE (mg/kg) | RATS | VOLUME | pH | TOTAL ACIDITY |
|---|---|---|---|---|---|
| Example 1, (b) product | 1 | 4 | ↑ 1% | ↑ 16% | ↑ 14% |
|  |  | 5 | ↓ 15% | ↑ 50% | ↓ 13% |
|  | 3 | 5 | ↓ 30% | ↑ 25% | ↓ 58% |
|  | 10 | 5 | ↓ 46% | ↑ 83% | ↓ 81% |
|  |  | 5 | ↓ 57% | ↑ 313% | ↓ 82% |
|  |  | 8 | ↓ 2.9% | ↑ 163% | ↓ 41% |
|  | 25 | 5 | ↓ 62% | ↑ 170% | ↓ 85% |
| Ranitidine | 1 | 4 | ↓ 46.2% | ↑ 17% | ↓ 38% |
|  |  | 5 | ↑ 6% | ↑ 60% | ↓ 18% |
|  | 3 | 5 | ↓ 5% | ↑ 46% | ↓ 47% |
|  | 10 | 5 | ↓ 30% | ↑ 95% | ↓ 66% |
|  |  | 5 | ↓ 58% | ↑ 202% | ↓ 75% |
|  |  | 8 | ↓ 12% | ↑ 97.4% | ↓ 50% |
|  | 25 | 5 | ↓ 55% | ↑ 210% | ↓ 83% |
| Cimetidine | 1 | 4 | ↓ 14% | ↑ 46% | ↓ 48% |
|  | 3 | 4 | ↓ 23% | ↑ 29% | ↓ 48% |
|  | 10 | 4 | ↓ 28% | ↑ 50% | ↓ 84% |
|  |  | 4 | ↓ 51% | ↑ 178% | ↓ 82% |
|  |  | 8 | ↓ 6.6% | ↑ 100% | ↓ 40% |
|  | 25 | 5 | ↓ 35.4% | ↑ 110% | ↓ 51.5% |

From the results obtained, it is seen that the activity of the Example 1, (b) product after intravenous and intraduodenal treatment is very high, with a reduction in the volume and an increase in the pH of the gastric juice. When compared with ranitidine, the Example 1, (b) product is seen to have practically the same activity when administered intraduodenally and rather higher when administered intravenously. The Example 1, (b) product is more active than cimetidine, both intraduodenally and intravenously.

Acute Toxicity

The acute toxicity of the Example 1, (b) product in rats and mice is low, as shown in the following table:

| SPECIES | ADMINISTRATION | LD$_{50}$ (mg/kg) |
|---|---|---|
| Rat | Oral | >10.000 |
| Mouse | Oral | >6.000 |
| Mouse | Intravenous | 200 mg/kg |

What we claim is:

1. Furan derivatives having the general formula:

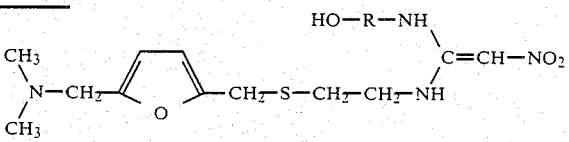

(I)

and the acid addition salts thereof with pharmaceutically acceptable acids, where R is a straight or branched alkylene chain of 1 to 6 carbon atoms.

2. The furan derivatives of claim 1, wherein, when R is —CH$_2$—CH$_2$—, the general formula is:

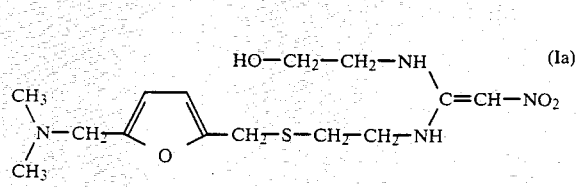

3. The furan derivatives of claim 2, wherein the product is N-[2-[[(5-[(dimethylamino)methyl]-2-furanyl)methyl]thio]ethyl]-N'-(2-hydroxyethyl)-2-nitro-1,1-ethenediamine.

4. A pharmaceutical composition for the treatment of gastroduodenal ulcer and all syndromes sustained or accompanied by acid secretion, comprising an active ingredient in amounts effective for applications selected from the compounds of any one of claims 1 to 3, associated with vehicles and/or other pharmaceutically acceptable active ingredients.

5. The pharmaceutical composition of claim 4, further having the active ingredient in a form appropriate for oral or parenteral administration.

* * * * *

UNITED STATES PATENT AND TRADEMARK OFFICE
CERTIFICATE OF CORRECTION

PATENT NO. : 4,515,806
DATED : May 7, 1985
INVENTOR(S) : Jose M. Caldero Ges and Eusebio M. Faba It is certified that error appears in the above-identified patent and that said Letters Patent are hereby corrected as shown below:

The structural formula identified by Roman numeral I and appearing above line 55 of column 1 and the structural formula Roman number I appearing above line 53 of column 2 are overprinted upon one another and should appear as follows:

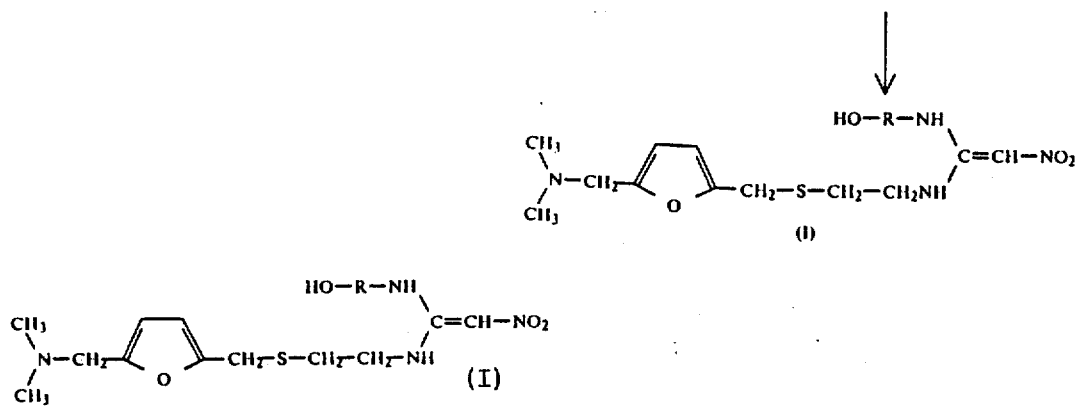

[SEAL]

Signed and Sealed this

Fifteenth Day of October 1985

Attest:

DONALD J. QUIGG

Attesting Officer

Commissioner of Patents and
Trademarks—Designate